United States Patent [19]

Engelhardt et al.

[11] Patent Number: 5,049,158
[45] Date of Patent: Sep. 17, 1991

[54] ACETABULAR CUP ASSEMBLY

[75] Inventors: John A. Engelhardt; Jon C. Serbousek; C. Wayne Allen, all of Warsaw; Alex M. DiNello, Fort Wayne; Jeff M. Ondrla; Duane G. Snyder, both of Warsaw, all of Ind.

[73] Assignee: Boehringer Mannheim Corporation, Indianapolis, Ind.

[21] Appl. No.: 511,457

[22] Filed: Apr. 20, 1990

[51] Int. Cl.⁵ .......................... A61F 2/34; B23B 45/12
[52] U.S. Cl. ........................................ 623/22; 403/326
[58] Field of Search ...................... 623/16, 18, 22, 23; 403/326

[56] References Cited

U.S. PATENT DOCUMENTS

| | | | |
|---|---|---|---|
| Re. 28,895 | 7/1976 | Noiles | 623/22 |
| 3,698,017 | 10/1972 | Scales et al. | 623/22 |
| 3,806,960 | 4/1974 | Weber | 623/22 |
| 4,051,559 | 10/1977 | Pifferi | 623/22 |
| 4,172,296 | 10/1979 | D'Errico | 623/22 |
| 4,365,358 | 12/1982 | Judet et al. | 623/22 |
| 4,380,090 | 4/1983 | Ramos | 623/22 |
| 4,408,360 | 10/1983 | Keller | 623/22 |
| 4,619,658 | 10/1986 | Pappas et al. | 623/22 |
| 4,623,352 | 11/1986 | Oh | 623/22 |
| 4,624,674 | 11/1986 | Pappas et al. | 623/22 |
| 4,645,180 | 2/1987 | Bregman et al. | 403/326 |
| 4,650,491 | 3/1987 | Parchinski | 623/22 |
| 4,678,472 | 7/1987 | Noiles | 623/22 |
| 4,695,282 | 9/1987 | Forte et al. | 623/22 |
| 4,795,469 | 1/1989 | Oh | 623/22 |
| 4,795,470 | 1/1989 | Goymann et al. | 623/22 |

FOREIGN PATENT DOCUMENTS 0066092 12/1982 European Pat. Off. ............. 623/22

OTHER PUBLICATIONS

"The Total System", Zimmer, Inc., Rev. 2/15 MI, 1984.

Primary Examiner—David J. Isabella
Attorney, Agent, or Firm—Barnes & Thornburg

[57] ABSTRACT

A prosthetic acetabular cup assembly includes a single piece bearing component having an inner bearing surface for receiving a ball attached to a femoral prosthesis and an outer surface. The assembly also includes a shell component for attachment to an acetabulum to replace a natural hip socket includes an inner surface defining a cavity for receiving the bearing component therein. The inner surface of the shell component is formed to include an arcuate groove therein. A formed wire is situated in the arcuate groove of the shell component. The wire is configured so that a portion of the wire extends radially inwardly from the arcuate groove of the shell component to engage an arcuate groove formed in the bearing component to retain the bearing component inside the shell component. Anti-rotation lugs are formed on the inner surface of the shell component to cut into the outer surface of the bearing component as the bearing component is inserted into the shell component to prevent rotation of the bearing component relative to the shell component.

26 Claims, 3 Drawing Sheets

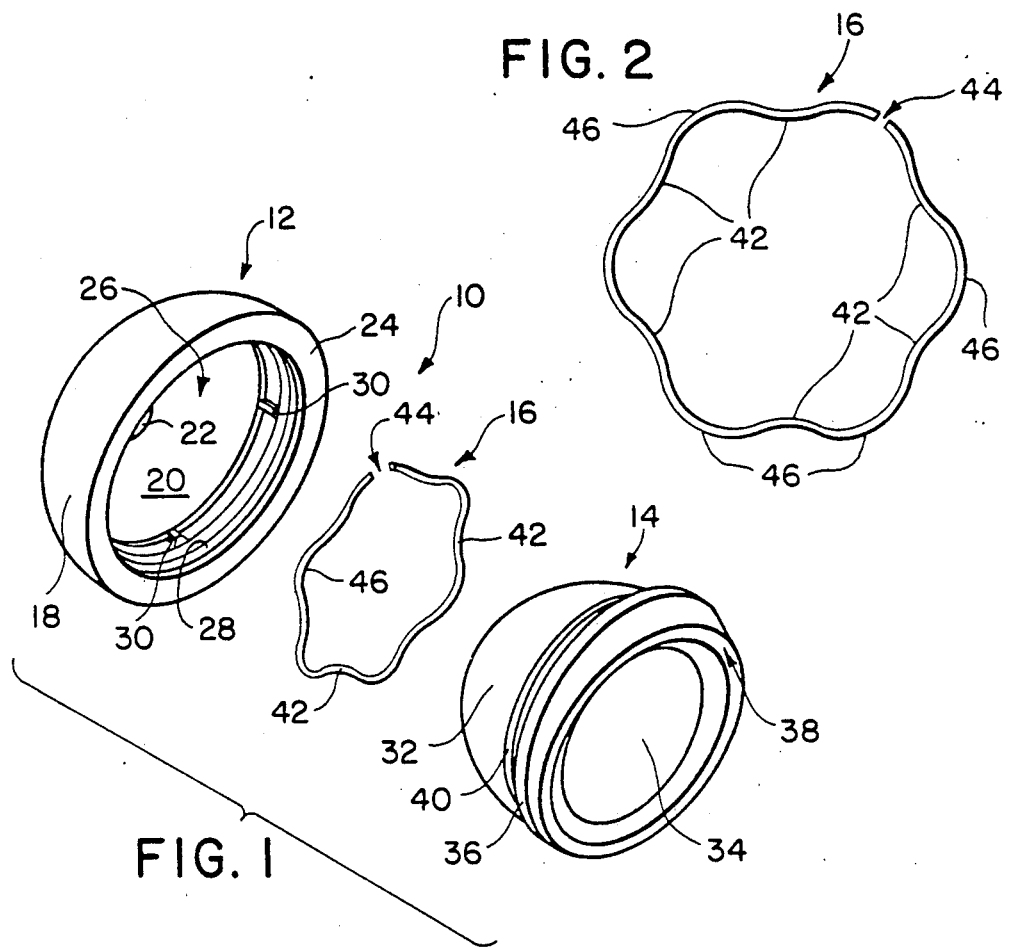
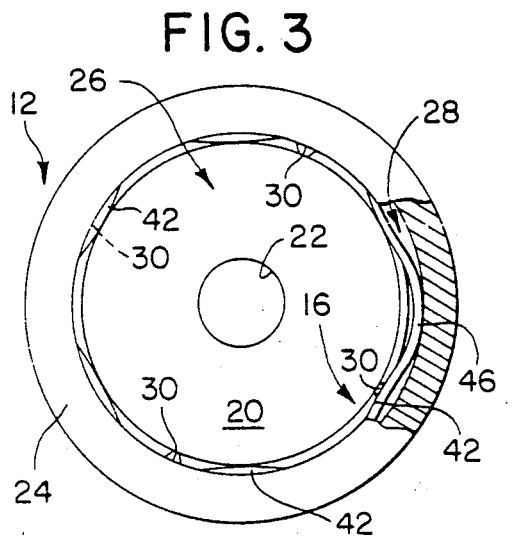
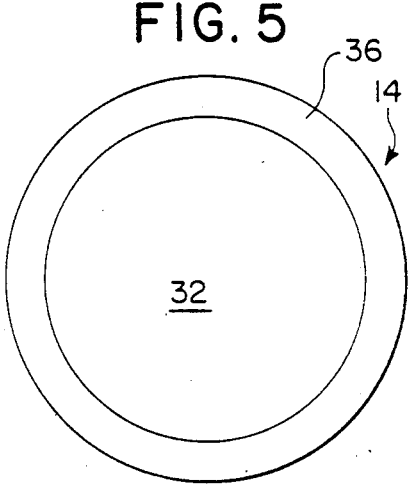

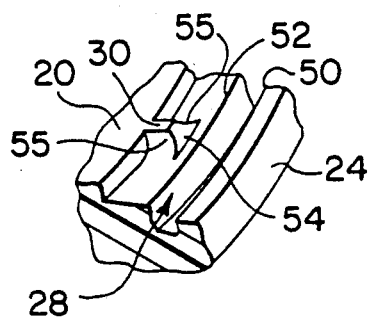
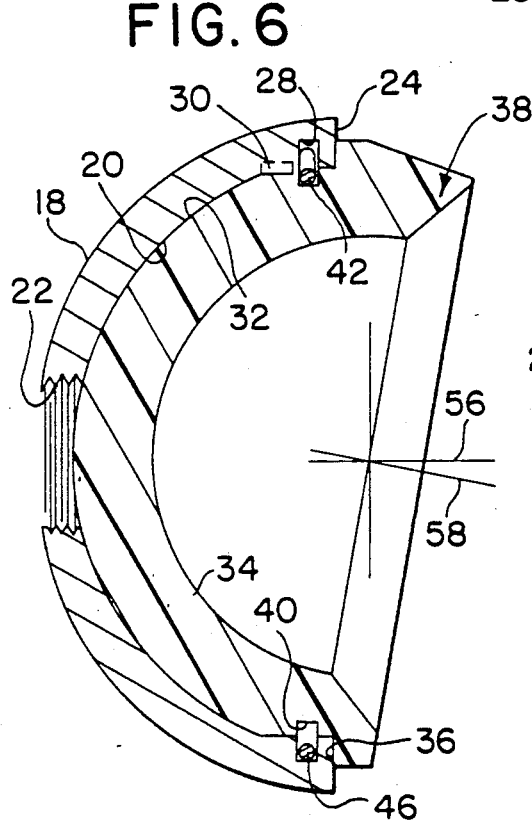
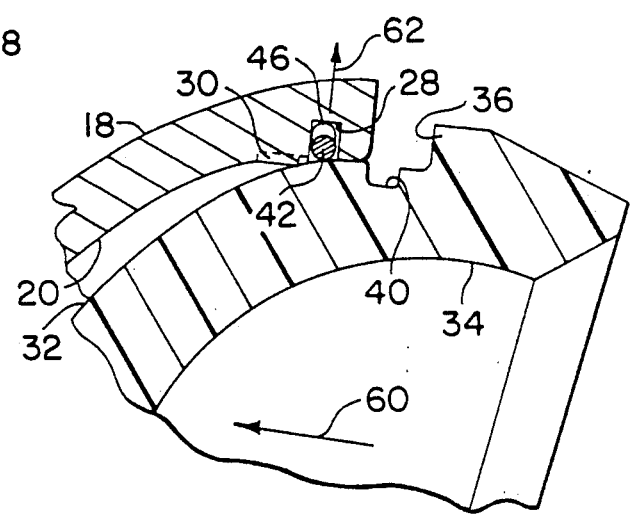
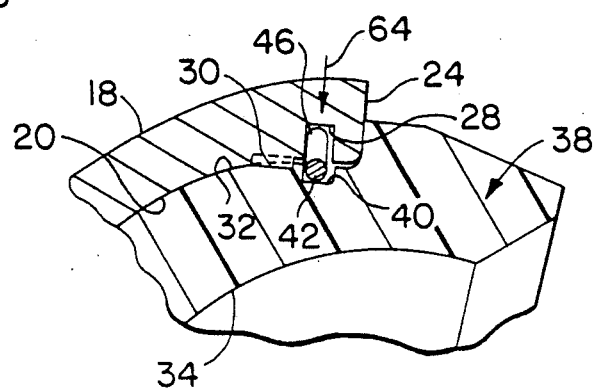

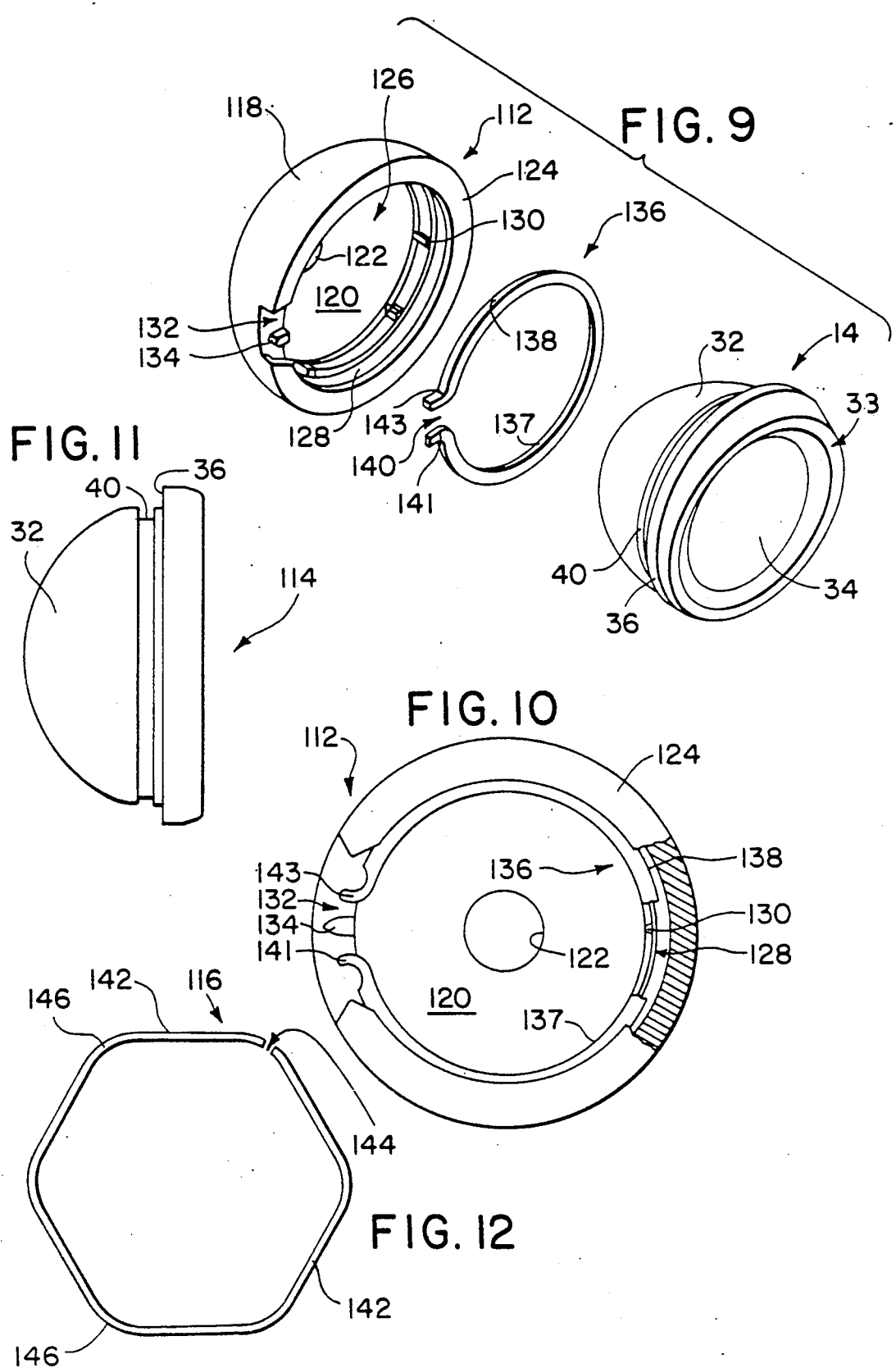

ACETABULAR CUP ASSEMBLY

BACKGROUND AND SUMMARY OF THE INVENTION

The present invention relates to hip prosthesis assemblies for replacing a natural hip socket. More particularly, the present invention relates to an acetabular cup assembly designed to retain a polymeric bearing inside an acetabular metal shell without the use of attachment screws.

It is known to provide an acetabular cup assembly including a metal shell component for attachment to an acetabulum to replace the natural socket and a polymer bearing component which is inserted into the shell to provide a hemispherical bearing surface for receiving a femur ball prosthesis element. Often, the polymer bearing component is nonsymmetrical and includes a built-up lip around a portion of the hemispherical bearing surface to help prevent dislocation of an installed femur ball from the hemispherical bearing surface. During installation of the acetabular cup assembly, the shell component is first secured to the acetabulum. When a surgeon installs the bearing component, the surgeon selects an orientation of the bearing with respect to the shell component to align the lip of the nonsymmetrical bearing component in the most advantageous position to reduce the likelihood of dislocation of the femur ball. Therefore, it is desirable to produce an acetabular cup assembly in which the bearing component can be attached to the shell component in a large number of selected orientations to provide the maximum degree of flexibility for the surgeon. An installed bearing component must be secured to a shell component by a retention force strong enough to prevent dislocation of the bearing component from the shell component.

One object of the present invention is to provide a retention mechanism for retaining a bearing component situated at any selected orientation inside a shell component which does not rely on the physical properties of the bearing component.

Another object of the present invention is to reduce loading of forces on an outer lip or flange of the bearing component after the hip prosthesis is installed in a patient.

Still another object of the present invention is to prevent rotation of the bearing component relative to the shell component after insertion of the bearing component into the shell component in a desired orientation.

A further object of the present invention is to provide a self adjusting locking mechanism which retains the bearing component inside the shell component despite possible shrinkage of the bearing component after installation.

According to the present invention, a prosthetic acetabular cup assembly is provided for receiving a ball attached to a femoral prosthesis. The assembly includes a bearing component having an inner bearing surface for receiving the ball and an outer surface. The assembly also includes a shell component for attachment to an acetabulum to replace a natural hip socket. The shell component includes an inner surface defining a cavity for receiving the bearing component therein. The inner surface of the shell component is formed to include an arcuate groove therein. The assembly further includes means located in the arcuate groove of the shell component for engaging the bearing component to retain the bearing component inside the shell component upon insertion of the bearing component to the shell component.

In one preferred embodiment of the present invention, the bearing component includes an arcuate groove formed in the outer surface. The arcuate groove of the bearing component is positioned on the outer surface of the bearing component in a position axially aligned with the arcuate groove of the shell component upon full insertion of the bearing component into the shell component. The engaging means includes a formed wire located inside the arcuate groove of the shell component. The wire is configured so that a portion of the wire extends radially inwardly from the arcuate groove of the shell component to lie within the arcuate groove of the bearing component. Therefore, the wire engages the bearing component to retain the bearing component inside the shell component. In an alternate embodiment, an expandable lock ring can be used in place of the wire to secure the bearing component to the shell component.

One feature of the present invention is the provision of a lock wire or lock ring situated inside an arcuate groove formed in the inner surface of the shell component. The shell component is typically made from metal such as titanium. Therefore, the position of the wire or lock ring is accurately maintained during insertion of the bearing component into the shell component. This prevents shifting of the axial position of the wire or lock ring relative to the shell component and ensures that the wire or lock ring will be properly aligned with the arcuate groove formed in the outer surface of the bearing component to retain or "lock" the bearing component in place upon insertion of the bearing component into the shell component.

Another feature of the present invention is the provision of anti-rotation lugs formed on the inner surface of the shell component. The lugs are situated below the arcuate groove formed in the inner surface of the shell component. The lugs interfere or machine into the outer surface of the bearing component as the bearing component is inserted into the shell component to prevent rotation of the bearing component relative to the shell component. There are no preformed slots in the bearing component for receiving the lugs. This feature advantageously provides no clearance or tolerance between the lugs and the outer surface of the bearing. Torsional backlash can occur if there is any clearance or tolerance between the lug and a preformed notch in the bearing component. Torsional backlash occurs when a force is exerted on the bearing component after installation of the assembly into the patient which causes slight movement of the bearing component. Therefore, the present invention reduces torsional backlash by providing no clearance or tolerance between the lugs and notches formed in the bearing.

Yet another feature of the present invention is that the locking mechanism permits "infinite dialability" of the bearing component with respect to the shell component while maintaining its ability to lock the bearing component inside the shell component. Bearing components are often nonsymmetrical and include a lip portion which aids in the retention of a femur ball within the bearing component. The locking mechanism of the present invention advantageously permits the surgeon to align the bearing component at any one of a continuum of positions relative to the shell component and then lock the bearing component in that position. This gives the surgeon greater flexibility when installing the assembly and allows the surgeon to select the precise orientation of the bearing component which is most advantageous to the patient.

Still another feature of the present invention is the provision of a shell component having an inner surface which is congruent with an outer surface of the bearing component. Advantageously, this congruency prevents loading on the lip or flange surrounding the bearing component. Such lip loading can occur when the femur ball exerts forces on the bearing component and the bearing component is not congruent with the shell component.

A further feature of the present invention is the provision of a locking mechanism which is capable of adjusting itself to compensate for changes which can occur in the bearing component. Because the bearing component is made from a polymeric material, its size can change over time. Often, bearing components show a propensity to shrink slightly over time after installation. Advantageously, the lock ring or wire of the present invention directs a retaining force radially inwardly into the cavity from the inner surface of the shell component and toward the bearing component. Therefore, if the arcuate groove in the bearing gets deeper due to wear over time or the bearing component shrinks after installation, the lock ring or wire can move radially inwardly to compensate for such changes in the bearing component.

Additional objects, features, and advantages of the invention will become apparent to those skilled in the art upon consideration of the following detailed description of a preferred embodiment exemplifying the best mode of carrying out the invention as presently perceived.

BRIEF DESCRIPTION OF THE DRAWINGS

The detailed description particularly refers to the accompanying figures in which:

FIG. 1 is an exploded perspective view of a preferred embodiment of the present invention illustrating an acetabular cup assembly including a lock wire positioned between a shell component and a bearing component;

FIG. 2 is a plan view illustrating the configuration of a preferred embodiment of the lock wire;

FIG. 3 is a plan view with portions broken away illustrating the lock wire situated inside an arcuate groove formed in the shell component;

FIG. 4 is an enlarged perspective view of a portion of the shell component illustrating the position of an anti-rotation lug relative to the arcuate groove formed in the inner surface of the shell component;

FIG. 5 is a plan view illustrating the configuration of the outer surface and flange of the bearing component;

FIG. 6 is a sectional view of the assembled acetabular cup illustrating the bearing component situated within the shell component and the lock wire inside both the arcuate groove formed in the shell component and the arcuate groove formed in the bearing component to lock the bearing component in place within the shell component;

FIG. 7 is an enlarged sectional view illustrating the position of the lock wire and an anti-rotation lug upon partial insertion of the bearing component into the shell component;

FIG. 8 is an enlarged sectional view similar to FIG. 7 illustrating the position of the lug and the lock wire after the bearing component is fully inserted into the shell component;

FIG. 9 is an exploded perspective view of a second preferred embodiment of the present invention illustrating a lock ring situated between a shell component and a bearing component;

FIG. 10 is a plan view with portions broken away of the shell component shown in FIG. 9 illustrating the lock ring situated inside an arcuate groove of the shell component;

FIG. 11 is an elevational view of a symmetrical bearing component that can be used with the present invention; and FIG. 12 is a plan view of another embodiment of the lock wire which can be used with the acetabular cup assembly of the present invention.

DETAILED DESCRIPTION OF THE DRAWINGS

Referring now to the drawings, FIG. 1 illustrates an acetabular cup assembly 10 of the present invention. The assembly 10 includes a shell component 12 designed to be affixed to the acetabulum to replace the natural hip socket and a bearing component 14 designed to be inserted into shell component 12. A lock wire 16 is also provided to retain the bearing component 14 within the shell component 12. The shell component 12 includes an outer surface 18 which can be textured to facilitate securing the shell component 12 in place within an appropriately prepared acetabulum. Shell component 12 is preferably made from titanium, but may be made from a cobalt chrome material. Shell component 12 also includes a generally hemispherically shaped inner surface 20. A threaded aperture 22 is also formed in the shell component 12 for receiving an appropriate tool (not shown) to remove the shell component 12 from the acetabulum. Shell component 12 further includes a lip or rim 24. The rim 24 defines a plane through which bearing component 14 enters cavity 26 of shell component 12 formed by inner surface 20. Inner surface 20 of shell component 12 is formed to include an arcuate groove 28 therein. In a preferred embodiment of the present invention, arcuate groove 28 extends around the entire periphery of cavity 26 spaced apart from rim 24 by a predetermined distance. It is possible, however, that arcuate groove 28 could be formed to extend only partially around the periphery and at varying depths in inner surface 20. More than one of these arcuate grooves which extend only partially around the periphery can be provided.

Shell component 12 is also formed to include anti-rotation lugs 30 on inner surface 20 of shell component 12. In selecting the number of lugs 30 to be used, there is a trade off between the insertion force required to insert bearing component 14 into shell component 12 and the rotational torque resistance that the lugs 30 provide. Each lug 30 added to shell component 12 increases the insertion force required but also increases the rotational torque resistance. Additionally, the depth of lugs 30 engagement into the bearing component 14 can be varied to adjust inversely the insertional force and rotational torque resistance. The preferred number of lugs 30, determined by balancing these factors, is four lugs 30 for each shell component 12. It is understood, however, that any number of lugs 30 can be used.

Bearing component 14 includes a generally hemispherically shaped outer surface 32 which is congruent or complimentary to inner surface 20 of shell component 12. Bearing component 14 also includes an inner bearing surface 34 for receiving a prosthetic femoral ball (not shown) and a radially outwardly projecting lip or flange 36 extending circumferentially around the bearing component 14. The bearing component 14 illustrated in the FIGS. 1-8 is a nonsymmetrical bearing component. It is understood, however, that the bearing component of the present invention may be a symmetrical component such as the bearing component 114 illustrated in FIG. 11. Bearing component 14 shown in FIGS. 1-8 includes a built-up lip portion 38 extending away from the flange 36 to aid in the retention of the femur ball inside bearing surface 34. Bearing component 14 is also formed to include radially outwardly opening arcuate groove 40 spaced apart from flange 36 by the same predetermined distance that arcuate groove 28 is spaced apart from rim 24. Bearing component 14 is preferably made from a polymeric material such as ultra high molecular weight polyethylene (UHMWPE). Of course, the bearing component 14 could be made of other types of implantable bearing material.

A preferred embodiment for lock wire 16 is illustrated in FIG. 2. Lock wire 16 is a serpentine shaped wire which is preferably made from cobalt chrome material and shaped by conventional wire forming techniques. Titanium may also be used to make wire 16. The lock wire 16 shown in FIGS. 1 and 2 has a somewhat hexagonal shape and includes six engaging sections 42. The wire 16 can be either serpentine shaped as shown in FIGS. 1 and 2 or polygon shaped having any number of sides. A gap 44 is provided between two adjacent sections 42 of lock wire 16 to permit lock wire 16 to expand radially outwardly. Corner portions 46 are situated between the side sections 42. The wire 16 may be conventionally heat treated to increase its strength.

Lock wire 16 is inserted into the arcuate groove 28 of shell component 12 as illustrated in FIG. 3. Corner portions 46 remain inside arcuate groove 28 to retain lock wire 16 inside arcuate groove 28. The configuration of the arcuate groove 28 is best shown in FIG. 4. The arcuate groove 28 includes an upper edge 50 spaced apart from rim 24 and a lower edge 52. Upper edge 50 and lower edge 52 define the arcuate groove 28 therebetween. Each of the four anti-rotation lugs 30 includes a top face 54 and edges 55 which interfere or machine into the outer surface 32 of bearing component 14 upon insertion of bearing component 14 into shell component 12. Lugs 30 are spaced apart from lower edge 52 by a predetermined distance as shown in FIG. 4. This gap between top face 54 of lug 30 and lower edge 52 of arcuate groove 28 provides a region to accommodate pieces of the bearing component 14 which are cut from outer surface 32 by lugs 30.

After shell component 12 is affixed to an appropriately prepared acetabulum, outer surface 32 of bearing component 14, as best illustrated in FIG. 5, is inserted into cavity 26 of shell component 12. The assembled acetabular cup assembly 10 is illustrated in FIG. 6. Shell component 12 includes an axis of symmetry 56 and the cavity defined by inner surface 34 of bearing component 14 includes an axis of symmetry 58. When the bearing component 14 is fully inserted into the shell component 12, axis of symmetry 58 is aligned at an angle with respect to axis of symmetry 56 of shell component 12 to aid in the retention of a femur ball (not shown) within a cavity defined by inner surface 34 of bearing component 14.

FIGS. 7 and 8 illustrate the operation of lock ring 16 and anti-rotation lugs 30 during insertion of bearing component 14 into shell component 12. FIG. 7 illustrates the bearing component 14 in a partially inserted position. Outer surface 32 of bearing component 14 engages the sections 42 of lock wire 16. As bearing component 14 is inserted in the direction of arrow 60, outer surface 32 of bearing component 14 applies a radially outwardly directed force on sections 42 of lock wire 16 to move sections 42 into arcuate groove 28 in the direction of arrow 62. In addition, when bearing component 14 is inserted to the position shown in FIG. 7, anti-rotation lugs 30 begin to interfere or machine into outer surface 32 of bearing component 14.

FIG. 8 illustrates the bearing component 14 in its fully inserted position. In the fully inserted position, arcuate groove 40 of bearing component 14 is axially aligned with arcuate groove 28 formed in shell component 12. When arcuate groove 40 of bearing component 14 is aligned with arcuate groove 28 of shell component 12, engaging sections 42 move in the direction of arrow 64 to lie within arcuate groove 40 of bearing component 14. Each section 42 applies a radially inwardly directed force to the bearing component 14 to retain sections 42 in arcuate groove 40 to hold the bearing component 14 in place with shell component 12. When bearing component 14 is fully inserted, lugs 30 have machined notches in the outer surface 32 of bearing component 14 to engage the bearing component 14 to prevent rotation of bearing component 14 with respect to shell component 12 about axis 56. Therefore, no clearance or tolerance exists between lugs 30 and the notches cut in the outer surface 32 of bearing component 14. This reduces torsional backlash forces on the bearing component 14 after installation. Once side sections 42 of lock wire 16 snap into place within arcuate groove 40 of bearing component 14, bearing component 14 is locked within shell component 12.

Since there are no preformed notches in outer surface 32 of bearing component 14 to receive lugs 30, the bearing component 14 can be inserted into shell component 12 at any desired orientation not limited by such preformed notches. Lock wire 16 therefore retains bearing component 14 inside shell component 12 regardless of the position of bearing component 14 relative to shell component 12. This maximizes a surgeon's flexibility to position the bearing component 14 in the most advantageous position relative to shell component 12 to reduce the likelihood that a femur ball (not shown) will become dislodged from the cavity defined by inner surface 34.

As shown in FIG. 6, outer surface 32 of bearing component 14 is congruent with inner surface 20 of shell component 12. There are no gaps or spaces between outer surface 32 and inner surface 20. By eliminating these gaps, the present assembly 10 reduces lip loading which can occur after the assembly 10 is installed in a patient if gaps remain between the outer surface 32 of bearing component 14 in the inner surface 20 of shell component 12.

FIG. 12 illustrates an alternate embodiment of a lock wire 116 which may be used with the present invention. Lock wire 116 includes relatively straight side sections 142, a gap 144, and corner sections 146. Corner sections 146 are configured to be situated inside arcuate groove 28 of shell component 12. Side sections 142 enter arcuate groove 40 formed in bearing component 14 to retain bearing component 14 inside shell component 12 upon insertion of bearing component 14 into shell component 12 in a manner similar to lock wire 16 shown in FIGS. 1–8.

Another embodiment of the present invention is illustrated in FIGS. 9 and 10. This embodiment uses the same bearing component 14 as in the first embodiment shown in FIGS. 1–8. Bearing component 114 shown in FIG. 11 may also be used in this embodiment. As best shown in FIG. 9, shell component 112 includes an outer surface 118 configured to be attached to a properly prepared acetabulum. Shell component 112 also includes a generally hemispherically shaped inner surface 120 having threaded aperture 122 formed therein. Shell component 112 further includes a lip or rim 124. The rim 124 defines a plane through which bearing component 14 enters cavity 126 of shell component 112 formed by inner surface 120. Inner surface 120 is formed to include an arcuate groove 128 which extends around the periphery of cavity 126 spaced apart from the rim 124 by the same predetermined distance that arcuate groove 28 is spaced apart from rim 24 in the first embodiment shown in FIGS. 1–8. Shell component 112 is also formed to include anti-rotation lugs 130 on inner surface 120 spaced equal distances apart. A notched section 132 of shell component 112 extends from arcuate groove 128 to rim 124. A blocking member 134 is formed in the notched section 132 of shell component 112.

A generally circular lock ring 136 is used to secure bearing component 14 to shell component 112. Lock ring 136 includes an inner edge 137 having an inner diameter and an outer edge 138 having an outer diameter. A gap 140 permits the lock ring 136 to expand and contract radially. Radially outwardly projecting arm members 141 and 143 retain lock ring 136 inside arcuate groove 128 of shell component 112.

As best shown in FIG. 10, arm members 141 and 143 are positioned in notched section 132 of shell component 112 on opposite sides of blocking member 134. When in its normal unexpanded configuration, the inner diameter of lock ring 136 is less than the diameter of cavity 126 taken at the position of arcuate groove 128. The outer diameter of lock ring 136 is larger than the diameter of the cavity 126 taken at the position of arcuate groove 128. Therefore, in its normal unexpanded configuration, lock ring 136 is retained within arcuate groove 128 of shell component 112. As bearing component 14 is inserted into shell component 112, outer surface 132 forces lock ring 136 to expand radially outwardly to lie totally with arcuate groove 128. Once arcuate groove 40 of bearing component 14 is aligned with arcuate groove 128 of shell component 112, lock ring 136 moves radially inwardly into arcuate groove 40 of bearing component 14 to retain bearing component 14 in place inside shell component 112. Therefore, lock ring 136 works in a manner similar to lock wires 16 and 116.

Lugs 130 cut or wedge themselves into outer surface 32 of bearing component 14 as bearing component 14 is inserted into shell component 112. Once the bearing component 14 is fully inserted, lugs 130 prevent rotation of bearing component 14 relative to shell component 112.

Although the invention has been described in detail with reference to several preferred embodiments, variations and modifications exist within the scope and spirit of the invention as described and defined in the following claims.

What is claimed is:

1. A prosthetic acetabular cup assembly for receiving a ball attached to a femur, the assembly comprising
    a bearing component including an inner bearing surface for receiving the ball and an outer surface,
    a shell component for attachment to an acetabulum to replace a natural hip socket, the shell component including an inner surface defining a cavity for receiving the bearing component therein, the inner surface of the shell component being formed to include an arcuate groove therein,
    means located in the arcuate groove of the shell component for engaging the bearing component to retain the bearing component inside the shell component upon insertion of the bearing component into the shell component, and
    means formed on the inner surface of the shell component for cutting into the outer surface of the bearing component as the bearing component is inserted into the shell component to prevent rotation of the bearing component relative to the shell component.

2. The assembly of claim 1, wherein the bearing component includes an arcuate groove formed in the outer surface thereof at a location that is axially aligned with the arcuate groove formed in the shell component upon insertion of the bearing component into the shell component and the engaging means includes a wire located inside the arcuate groove of the shell component, the wire being configured sot that a portion of the wire extends from the arcuate groove of the shell component to lie within the arcuate groove of the bearing component to retain the bearing component inside the shell component upon insertion of the bearing component into the shell component.

3. The assembly of claim 2, wherein the wire includes a plurality of first sections which extend from the arcuate groove of the shell component to lie inside the cavity of the shell component and a plurality of second sections located inside the arcuate groove of the shell component to hold the wire inside the arcuate groove formed in the shell component, the first sections being configured to enter the arcuate groove formed in the bearing component upon insertion of the bearing component into the shell component to engage the bearing component to retain the bearing component inside the shell component.

4. The assembly of claim 3, wherein the cutting means includes at least one lug formed on the inner surface of the shell component, the at least one lug being configured to interfere into the outer surface of the bearing component as the bearing component is inserted into the shell component to prevent rotation of the bearing component relative to the shell component after insertion of the bearing component into the shell component.

5. The assembly of claim 1, wherein the bearing is nonsymmetrically shaped and includes a radially outwardly projecting flange extending circumferentially around the bearing component and a lip portion formed on a portion of the flange to aid in the retention of the ball within the inner bearing surface, the bearing is rotatable with respect to the shell component prior to insertion of the bearing component into the shell component to align the lip portion of the bearing component in a selected one of a continuum of positions relative to the shell component, and the cutting means is configured to retain the bearing component inside the shell component when the bearing component is aligned at any one of the continuum of selected positions relative to the shell component to prevent rotation of the bearing component relative to the shell component upon insertion of the bearing component into the shell component.

6. The assembly of claim 1, wherein the cutting means includes at least one lug formed on the inner surface of the shell component, each lug being configured to cut a notch in the outer surface of the bearing component as the bearing component is inserted into the shell component to prevent rotation of the bearing component relative to the shell component after insertion of the bearing component into the shell component.

7. The assembly of claim 6, wherein the arcuate groove formed in he shell component includes upper and lower boundary edge, each lug includes a top surface for cutting into the outer surface of the bearing component, and the top surface of each lug is located below the arcuate groove formed in the shell component spaced apart from the lower boundary edge.

8. The assembly of claim 1, wherein the bearing component includes an arcuate groove formed in the outer surface thereof at a location that is axially aligned with the arcuate groove formed in the shell component upon insertion of the bearing component into the shell component and the engaging means includes a generally circular lock ring situated inside the arcuate groove of the shell component, the lock ring including an outer edge located inside the arcuate groove of the shell component to hold the lock ring within the arcuate groove formed in the shell component and including an inner edge configured to enter the arcuate groove of the bearing component to engage the bearing component and to retain the bearing component inside the shell component.

9. The assembly of claim 8, wherein the shell component includes an outer rim and a notched section extending from the arcuate groove formed in the shell assembly to the outer rim of the shell assembly and the lock ring includes first and second arm members extending radially outwardly from the lock ring, the arm members being located within the notched section of the shell component to retain the lock ring inside the arcuate groove of the shell component.

10. The assembly of claim 9, further comprising a blocking member formed in the notched section of the shell component, the arm members of the lock ring being situated on opposite sides of the blocking member so that the blocking member engages the arm members to prevent rotation of the lock ring relative to the shell component.

11. A prosthetic acetabular cup assembly for receiving a ball attached to a femur, the assembly comprising a bearing component including an inner bearing surface for receiving the femur ball, a generally hemispherically shaped outer surface, and a radially outwardly projecting flange extending circumferentially around the bearing component, the outer surface of the bearing being formed to include an arcuate groove therein spaced apart from the flange by a predetermined distance, a shell component for attachment to an acetabulum to replace a natural hip socket, the shell component including an inner surface defining a generally hemispherical cavity complementary to the outer surface of the bearing component for receiving the bearing component therein, and a rim for abutting the flange of the bearing component upon insertion of the bearing component into the shell component, the inner surface of the shell component being formed to include an arcuate groove extending around the periphery of the cavity spaced apart from the rim by said predetermined distance, a wire situated inside the arcuate groove of the shell component, the wire including a plurality of sections which extend from the arcuate groove of the shell component to lie inside the cavity of the shell component, said sections being configured to enter the arcuate groove formed in the outer surface of the bearing component upon insertion of the bearing component into the shell component to engage the bearing component to retain the bearing component inside the shell component, and means formed on the inner surface of the shell component for cutting into the outer surface of the bearing component as the bearing component is inserted into the shell component to prevent rotation of the bearing component relative to the shell component.

12. The assembly of claim 11, wherein the cutting means includes at least one lug formed on the inner surface of the shell component, each lug being configured to cut a notch in the outer surface of the bearing component as the bearing component is inserted into the shell component to prevent rotation of the bearing component relative to the shell component.

13. The assembly of claim 12, wherein the at least one lug is spaced apart from the arcuate groove formed in the inner surface of the shell component in a direction opposite the rim of the shell component to provide a region between at least one lug and the arcuate groove formed in the shell component to accumulate portions of the outer surface of the bearing component cut from the bearing component by the at least one lug.

14. The assembly of claim 11, wherein the bearing component is nonsymmetrically shaped and includes a lip portion extending away from a portion of the flange to aid in the retention of the ball within the inner bearing surface, the bearing component is rotatable with respect to the shell component prior to insertion of the bearing component into the shell component to align the lip portion of the bearing component in a selected one of a continuum of positions relative to the shell component, and the cutting means is configured to retain the bearing component inside the shell component when the bearing component is aligned in any selected one of the continuum of positions relative to the shell component to prevent rotation of the bearing component relative to the shell component upon insertion of the bearing component into the shell component.

15. A prosthetic acetabular cup assembly for receiving a ball attached to a femur, the assembly comprising a bearing component including an inner bearing surface for receiving the ball and on outer surface, a shell component for attachment to an acetabulum to replace a natural hip socket, the shell component including an inner surface defining a cavity for receiving the bearing component therein, a lug formed on the inner surface of the shell component, the lug being configured to cut into the outer surface of the bearing component as the bearing component is inserted into the shell component to prevent rotation of the bearing component relative to the shell component, and means for coupling the bearing component to the shell component to retain the bearing component inside the shell component upon insertion of the bearing component into the shell component.

16. The assembly of claim 15, wherein the inner surface of the shell component is formed to include an arcuate groove therein, the bearing component includes an arcuate groove formed in the outer surface thereof at a location that is axially aligned with the arcuate groove formed in the shell component upon insertion of the bearing component into the shell component and the coupling means includes a wire located inside the arcuate groove of the shell component, the wire being configured so that a portion of the wire extends form the arcuate groove of the shell component to lie within the arcuate groove of the bearing component to retain the bearing component inside the shell component upon insertion of the bearing component into the shell component.

17. The assembly of claim 16, wherein the wire includes a plurality of first sections which extend from the arcuate groove of the shell component to lie inside the cavity of the shell component and a plurality of second sections located inside the arcuate groove of the shell component to hold the wire inside the arcuate groove formed in the shell component, the first sections being configured to enter the arcuate groove formed in the bearing component upon insertion of the bearing component into the shell component to engage the bearing component to retain the bearing component inside the shell component.

18. The assembly of claim 15, wherein the bearing is nonsymmetrically shaped and includes a radially outwardly projecting flange extending circumferentially around the bearing component and a lip portion formed on a portion of the flange to aid in the retention of the ball within the inner bearing surface, the bearing is rotatable with respect to the shell component prior to insertion of the bearing component into the shell component to align the lip portion of the bearing component in a selected one of a continuum of positions relative to the shell component, and the assembly includes a plurality of lugs configured to cut a plurality of notches in the outer surface of the bearing component as the bearing component is inserted into the shell component.

19. The assembly o claim 16, wherein the arcuate groove formed in he shell component includes upper and lower boundary edges, the lug includes a top surface for interfering into the outer surface of the bearing component, and the top surface of the lug is located below the arcuate groove formed din the shell component spaced apart from the lower boundary edge.

20. The assembly of claim 15, wherein the inner surface of the shell component is formed to include an arcuate groove therein, the bearing component includes an arcuate groove formed in the outer surface thereof at a location that is axially aligned with the arcuate groove formed in the shell component upon insertion of the bearing component into the shell component and the coupling means includes a generally circular lock ring situated inside the arcuate groove of the shell component, the lock ring including an outer edge located inside the arcuate groove of the component to hold the lock ring within the arcuate groove formed in the shell component and including an inner edge configured to enter the arcuate groove of the bearing component to engage the bearing component and to retain the bearing component inside the shell component.

21. A prosthetic assembly for receiving a ball attached to a bone, the assembly comprising a bearing component including an inner bearing surface for receiving the ball and an outer surface, a shell component for attachment to an acetabulum to replace a natural hip socket, the shell component including an inner surface defining a cavity for receiving the bearing component therein, means for coupling the bearing component to the shell component to retain the bearing component inside the shell component upon insertion of the bearing component into the shell component, and means formed on the inner surface of the shell component for cutting into the outer surface of the bearing component as the bearing component is inserted into the shell component to prevent rotation of the bearing component relative to the shell component.

22. The assembly of claim 21, wherein the inner surface of the shell component is formed to include an arcuate groove therein and the bearing component includes an arcuate groove formed in the outer surface thereof at a location that is axially aligned with the arcuate groove formed in the shell component upon insertion of the bearing component into the shell component and the coupling means includes a wire located inside the arcuate groove of the shell component, the wire being configured so that a portion of the wire extends from the arcuate groove of the shell component to lie within the arcuate groove of the bearing component to retain the bearing component inside the shell component upon insertion of the bearing component into the shell component.

23. The assembly of claim 22, wherein the wire includes a plurality of first sections which extend from the arcuate groove of the shell component to lie inside the cavity of the shell component and a plurality of second sections located inside the arcuate groove of the shell component to hold the wire inside the arcuate groove formed in the shell component, the first sections being configured to enter the arcuate groove formed in the bearing component upon insertion of the bearing component into the shell component to engage the bearing component to retain the bearing component inside the shell component.

24. The assembly of claim 21, wherein the bearing is nonsymmetrically shaped and includes a radially outwardly projecting flange extending circunmferentially around the bearing component and a lip portion formed on a portion of the flange to aid in the retention of the ball within the inner bearing surface, the bearing is rotatable with respect to the shell component prior to insertion of the bearing component into the shell component to align the lip portion of the baring component in a selected one of a continuum of positions relative to the shell component, and the cuting means is configured to retain the bearing component inside the shell component when the bearing component is aligned at any one of the continuum of selected positions relative to the shell component to prevent rotation of the bearing component relative to the shell component upon insertion of the bearing component into the shell component.

25. The assembly of claim 22, wherein the arcuate groove formed in the shell component includes upper and lower boundary edges, and the cutting means includes a lug having a top surface for machining into the outer surface of the bearing component, and the top surface of the lug is located below the arcuate groove formed in the shell component spaced apart from the lower boundary edge.

26. The assembly of claim 21, wherein the inner surface of the shell component is formed to include an arcuate groove therein and the bearing component includes an arcuate groove formed in the outer surface thereof at a location that is axially aligned with the arcuate groove formed in the shell component upon insertion of the bearing component into the shell component and the coupling means includes a generally circular lock ring situated inside the arcuate groove of the shell component, the lock ring including an outer edge located inside the arcuate groove of the shell component to hold the lock ring within the arcuate groove formed in the shell component and including an inner edge configured to enter the arcuate groove of the bearing component to engage the bearing component and to retain the bearing component inside the shell component.

* * * * *